United States Patent
Mannheimer et al.

(10) Patent No.: US 6,801,797 B2
(45) Date of Patent: Oct. 5, 2004

(54) PULSE OXIMETER SENSOR WITH PIECE-WISE FUNCTION

(75) Inventors: Paul D. Mannheimer, Danville, CA (US); Michael E. Fein, deceased, late of Mountain View, CA (US); by Marcia Fein, legal representative, Danville, CA (US); Charles E. Porges, Orinda, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 0 days.

(21) Appl. No.: 09/836,050

(22) Filed: Apr. 16, 2001

(65) Prior Publication Data

US 2002/0035318 A1 Mar. 21, 2002

Related U.S. Application Data

(60) Provisional application No. 60/198,109, filed on Apr. 17, 2000.

(51) Int. Cl.[7] .............................................. A61B 5/00
(52) U.S. Cl. ...................................... 600/323; 600/331
(58) Field of Search ................................ 600/309–310, 600/322–324, 336, 331

(56) References Cited

U.S. PATENT DOCUMENTS

| | | | | |
|---|---|---|---|---|
| 4,086,915 A | * | 5/1978 | Kofsky et al. ............... | 600/330 |
| 4,623,248 A | * | 11/1986 | Sperinde ....................... | 356/41 |
| 4,942,877 A | * | 7/1990 | Sakai et al. .................. | 600/323 |
| 5,503,148 A | * | 4/1996 | Pologe et al. ................ | 600/323 |
| 5,987,343 A | | 11/1999 | Kinast .......................... | 600/323 |
| 6,104,938 A | * | 8/2000 | Huiku et al. ................. | 600/322 |

FOREIGN PATENT DOCUMENTS

| | | | | |
|---|---|---|---|---|
| EP | 0 571 225 A2 | | 11/1993 | |
| WO | WO 93/06775 | * | 4/1993 | ................. 600/364 |
| WO | WO 00/61000 | | 10/2000 | |

\* cited by examiner

*Primary Examiner*—Max F. Hindenburg
*Assistant Examiner*—Matthew Kremer
(74) *Attorney, Agent, or Firm*—Townsend and Townsend and Crew LLP

(57) ABSTRACT

A memory in a sensor is used to store multiple coefficients for a physiological parameter. In one embodiment, not only are the sensor's specific calibration coefficients stored in a memory in the sensor for the formula to determine oxygen saturation, but multiple sets of coefficients are stored. The multiple sets apply to different ranges of saturation values to provide a better fit to occur by breaking the R to SpO2 relationship up into different pieces, each described by a different function. The different functions can also be according to different formulas for determining oxygen saturation.

8 Claims, 4 Drawing Sheets

PULSE OXIMETER SENSOR WITH PIECE-WISE FUNCTION

BACKGROUND OF THE INVENTION

The present invention relates to oximeter sensors having a memory.

Pulse oximetry is typically used to measure various blood flow characteristics including, but not limited to, the blood-oxygen saturation of hemoglobin in arterial blood, and the rate of blood pulsations corresponding to a heart rate of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Various methods have been proposed in the past for coding information in sensors, including pulse oximeter sensors, to convey useful information to a monitor. For example, an encoding mechanism is shown in Nellcor U.S. Pat. No. 4,700,708. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary from device-to-device, a coding resistor is placed in the sensor with the value of the resistor corresponding to the actual wavelength of at least one of the LEDs. When the oximeter instrument is turned on, it first determines the value of the resistor and thus appropriate saturation calculation coefficients for the value of the wavelengths of the LEDs in the probe.

Other coding mechanisms have also been proposed in U.S. Pat. Nos. 5,259,381; 4,942,877; 4,446,715; 3,790,910; 4,303,984; 4,621,643; 5,246,003; 3,720,177; 4,684,245; 5,645,059; 5,058,588; 4,858,615; and 4,942,877, the disclosures of which are all hereby incorporated by reference. The '877 patent in particular discloses storing a variety of data in a pulse oximetry sensor memory, including coefficients for a saturation equation for oximetry.

Nellcor pulse oximeter sensors are encoded with a resistor (RCAL) value that corresponds to the wavelength of the red LED within the emitter, such as described in Pat. No. 4,700,708. Nellcor pulse oximeter instruments read this resistor coding value and use it as a pointer to a look-up table that holds the proper set of coefficients for that sensor for calculating arterial oxygen saturation ($SpO_2$). The function that converts the measured red and IR signal modulation ratio R (also known as the "ratio of ratios" or "rat-rat") to a calculated saturation value is derived from the basic form of the Lambert-Beer Law:

$$R = \frac{\ln(I_1/I_2)_{red}}{\ln(I_1/I_2)_{ir}} = \frac{S \cdot \beta_{O2Hb}^{red} + (1-S) \cdot \beta_{Hb}^{red}}{S \cdot \beta_{O2Hb}^{ir} + (1-S) \cdot \beta_{Hb}^{ir}} = \frac{S \cdot c_1 + (1-S) \cdot c_2}{S \cdot c_3 + (1-S) \cdot c_4} \quad (1)$$

where $I_1$ and $I_2$ refer to detected light signals at two different points in the cardiac cycle, and the $\beta$ s refer to the characteristic light absorption properties of oxygenated and deoxygenated hemoglobin. When solved for the saturation (S), the result takes on the form:

$$SpO_2 = S \cdot 100 = \frac{c_2 - c_4 \cdot R}{(c_3 - c_4) \cdot R + (c_2 - c_1)} \cdot 100. \quad (2)$$

Equation 2 can be further simplified to require only three constants (by, for example, dividing each constant by $c_2$), but will be used as shown for the remainder of this description. Although theoretically based, the four constants $c_1$–$c_4$ are empirically determined. Theoretical values for the constants are insufficient primarily due to the complexities of light scattering and sensor optics. The values of the sets of constants ($c_1$ through $c_4$) vary with each resistor coding bin (each "bin" corresponding to a range of different characterized LED wavelengths). Multiple sets of coefficients (bins) are provided within a lookup table in Nellcor oximeters. When calculated $SpO_2$ values according to Eq.2 are less than 70%, a revised value of $SpO_2$ using a linear function is used:

$$SpO_2 = c_5 - c_6 \cdot R, \quad (3)$$

where both $c_5$ and $c_6$ vary with the resistor coding value. This linear function was found to better match $SpO_2$ (arterial oxygen saturation as measured by a pulse oximeter) with $SaO_2$ (the true value of arterial oxygen saturation, as measured directly on a blood sample) in observations made at low saturations.

A limitation of this method is that the proper calibration of the pulse oximetry sensor can be accomplished only if the relationship between the signal modulation ratio (R) to blood $SaO_2$ conforms to one of the pre-encoded sets of calibration coefficients.

A further limitation of this method is that the relationship between R and $SaO_2$ of the pulse oximetry sensor may not be linear in a low-saturation region, or that the breakpoint may not optimally be located at 70% $SpO_2$.

A yet further limitation of this prior art method is that the functional relationship between the true arterial oxygen saturation and the measured signals may not fit a single function over the entire span of the measurement range.

SUMMARY OF THE INVENTION

The present invention takes advantage of a memory in the sensor to provide enhanced performance. In one embodiment, not only are the sensor's specific calibration coefficients stored in a memory in the sensor for the formula to determine oxygen saturation, but multiple sets of coefficients are stored. The multiple sets apply to different ranges of saturation values to provide a better fit to occur by breaking the R to SpO2 relationship up into different pieces, each described by a different function. The different functions can also be according to different formulas for determining oxygen saturation.

In another aspect of the invention, the sensor can store a variable breakpoint between the two functions used for oxygen saturation. The two functions could either be separate formulas or the same formula with different coefficients. This allows optimization to a value other than the 70% breakpoint of the prior art.

In another aspect of the present invention, the sensor can store more than one breakpoint to create more than two functions describing the R to SpO2 relationship.

In yet another aspect of the present invention, a spline function is used, breaking up the R to SpO2 relationship into an arbitrary number of regions.

In one embodiment, the coefficients stored in the sensor memory correspond to a non-linear curve for low saturation values below 70% or some other breakpoint(s).

Each of the methods described here improve the fit between the chosen mathematical function and the arterial oxygen saturation by breaking the relationship into subsets of the full measured range and determining optimum coefficients for each range. Spline-fitting, in this context, similarly breaks the full measurement range into subsets to efficiently describe the numerical relational between the underlying tissue parameter of interest and the actual signals being used to estimate its value.

For a further understanding of the nature and advantages of the invention, reference should be made to the following description taken in conjunction with the accompanying drawings.

DESCRIPTION OF THE SPECIFIC EMBODIMENTS

Sensor Reader/Monitor

Figure 1:
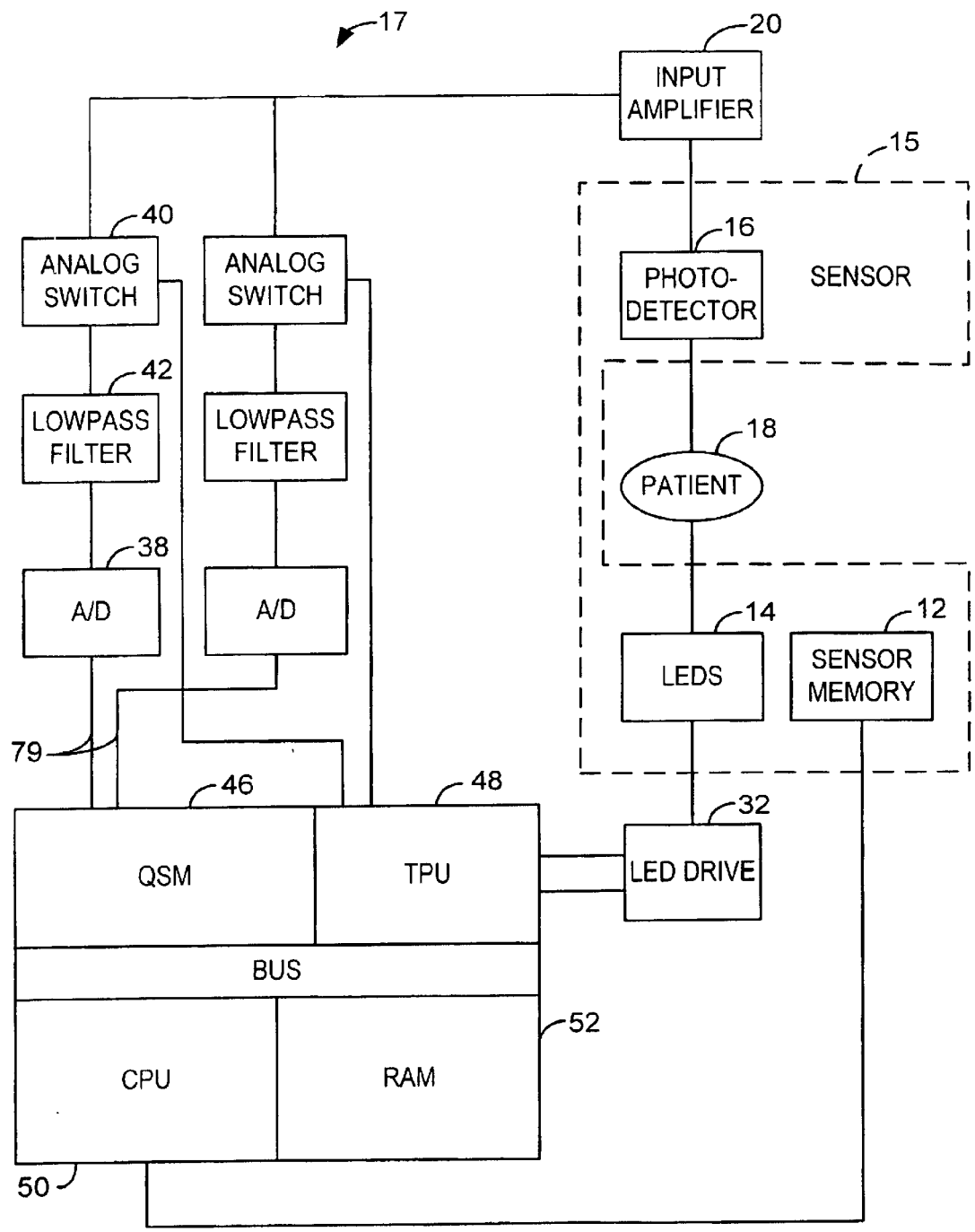
FIG. 1 is a block diagram of a pulse oximeter system incorporating the present invention.

FIG. 1 is a block diagram of one embodiment of the invention. FIG. 1 shows a pulse oximeter 17 (or sensor reader) which is connected to a non-invasive sensor 15 attached to patient tissue 18. Light from sensor LEDs 14 passes into the patient tissue 18, and after being transmitted through or reflected from tissue 18, the light is received by photosensor 16. Either two or more LEDs can be used depending upon the embodiment of the present invention. Photosensor 16 converts the received energy into an electrical signal, which is then fed to input amplifier 20.

Light sources other than LEDs can be used. For example, lasers could be used, or a white light source could be used with appropriate wavelength filters either at the transmitting or receiving ends.

Time Processing Unit (TPU) 48 sends control signals to the LED drive 32, to activate the LEDs, typically in alternation. Again, depending on the embodiment, the drive may control two or any additional desired number of LEDs.

The signal received from input amplifier 20 is passed through two different channels as shown in the embodiment of FIG. 1 for two different wavelengths. Alternately, three channels for three wavelengths could be used, or N channels for N wavelengths. Each channel includes an analog switch 40, a low pass filter 42, and an analog to digital (A/D) converter 38. Control lines from TPU 48 select the appropriate channel at the time the corresponding LED 14 is being driven, in synchronization. A queued serial module (QSM) 46 receives the digital data from each of the channels via data lines 79. CPU 50 transfers the data from QSM 46 into RAM 52 as QSM 46 periodically fills up. In one embodiment, QSM 46, TPU 48, CPU 50 and RAM 52 are part of one integrated circuit, such as a microcontroller.

Sensor Memory

Sensor 15, which includes photodetector 16 and LEDs 14, has a sensor memory 12 associated with it. Memory 12 is connected to CPU 50 in the sensor reader or monitor 17. The memory 12 could be packaged in a body of the sensor 15 or in an electrical plug connected to the sensor. Alternatively, the memory 12 could be packaged in a housing which is attachable to an external surface of the monitor or the memory 12 could be located anywhere in a signal path between the sensor body and the monitor. Specifically, according to some preferred embodiments, a content of the sensor memory 12 could be constant for all sensors associated with a particular sensor model. In this case, instead of putting an individual memory 12 on each sensor associated with this model, the memory 12 could instead be included in a reusable extension cable associated with the sensor model. If the sensor model is a disposable sensor, in this case a single memory 12 would be incorporated into a reusable extension cable. The reusable cable could then be used with multiple disposable sensors.

Figure 2:
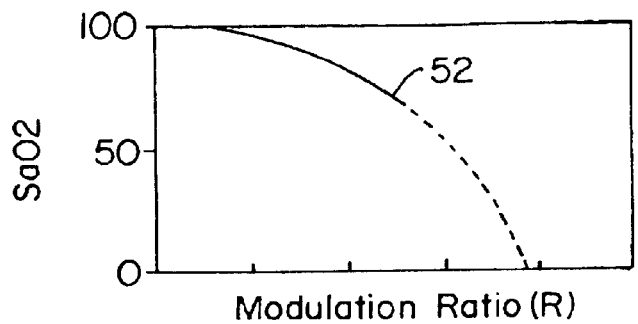
FIG. 2 is a graph of R (signal modulation ratio) versus oxygen saturation ($SaO_2$).

FIG. 2 is an example of a graph of the ratio of ratios (R) on the X axis versus oxygen saturation ($SaO_2$) on the Y axis. Shown is a breakpoint 52. In the prior art, a breakpoint of 70% was pre-defined in the monitor software. To the right of the breakpoint (oxygen saturations between 70–100%) a formula was used with four coefficients. To the left of the breakpoint in the prior art, a linear equation was used with two coefficients. The present invention provides increased flexibility and accuracy by using a non-linear formula for the portion of the curve to the left of breakpoint 52. By using a memory chip in the sensor itself, it is possible to actually store these coefficients on the memory chip, as well as the separate coefficients for the higher saturation values.

In another embodiment of the invention, breakpoint 52 can be stored in the memory chip, and chosen to optimize the curve fitting for the two sets of coefficients. In other words, a better fit to the two curves may be obtained if the breakpoint is 68%, for example. In an alternate embodiment, multiple breakpoints and curves might be used. In addition, rather than using the same formula, different formulas could be used for different sections in another embodiment.

Figure 3:
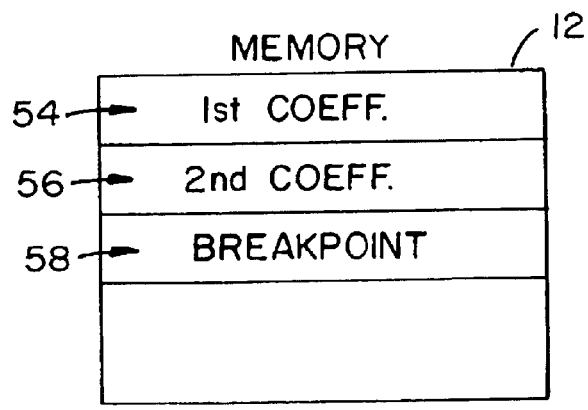
FIG. 3 is a diagram of the contents of a sensor memory according to the invention.

FIG. 3 illustrates the contents of sensor memory 12 of FIG. 1. As illustrated, in a first section of memory 54 are stored a first set of coefficients. A second portion of memory 56 stores a second set of coefficients. Finally, in a third section of memory 58, the breakpoint 52 is stored. Different combinations of these elements could be stored in different memories. For example, the breakpoint could be left out of some, and in others a breakpoint may be provided with only one set of coefficients (with the other set of coefficients in the monitor). Alternately, a breakpoint might be implied from a sensor model number which is stored in the memory, or some other ID value.

β-Equation

In one embodiment, an enhanced form of the curvilinear function is used. Instead of using Eq.3 (linear) in the lower saturation region, Eq.2 (non-linear) is used for both the upper and lower saturation regions. The breakpoint that defines when to switch coefficients from an upper-region set to a lower-region set is defined by another coefficient. The breakpoint can be programmed either as a value of R, or as a value of $SpO_2$. With the breakpoint defined as a value of R, the algorithm becomes:

$$SpO_2 = \frac{b-d \cdot R}{(c-d) \cdot R + (b-a)} \cdot 100 \begin{cases} R \leq c_5: & a = c_1, b = c_2, c = c_3, d = c_4 \\ R > c_5: & a = c_6, b = c_7, c = c_8, d = c_9 \end{cases} \quad (4)$$

Curve Fitting

Curve fitting to multiple regions follows the same methodology as fitting to a single region. Simply put, the data is partitioned into separate regions and coefficients are determined for each region separately. Commercially available software programs are available, (for example, Mathcad, (Mathsoft, Inc., Cambridge, Mass.). The process can also be found in, for example, Data Reduction and Error Analysis for the Physical Sciences (Philip Beviyton, McGraw-Hill, New York 1969, Ch.11—Least squares fit to an arbitrary function).

Spline Fitting

An alternate embodiment uses either spline (curve) fitting, or linear or higher order interpolation to a predefined set of $SpO_2$ vs R values ("knots"). A "knot" is a term of art in spline fitting that refers to an x-y pair corresponding to a node on a line, with a number of such knots defining the line. Spline fitting is a technique for interpolation.

For instance, the values of R at specifically defined $SpO_2$ values would be stored in the sensor memory. An example of this looks like:

| R = | a | b | c |
|---|---|---|---|
| $SpO_2 =$ | 100 | 95 | 90 |

Alternatively, though less preferably, the independent variable could be swapped:

| R = | 0.5 | 0.6 | 0.7 |
|---|---|---|---|
| $SpO_2 =$ | x | y | z | a) Only the bold values (e.g., a, b and c) would need to be stored with fixed, pre-selected spaced values of $SpO_2$ (equally spaced or unequally spaced). Or, alternatively, preselected values of R.
b) An alternative approach would store within the sensor memory the $SpO_2$(minimum) and $SpO_2$(maximum) values of the spline range, the number of knots that will be defined, and the sequence of defined values of R for those knots.
c) A further alternative approach could store both $SpO_2$ and the associated R value for each knot.

For each of these options, the instrument would use a spline-fitting algorithm, preferably a cubic spline, to determine the $SpO_2$ at the measured value of R according to the stored values (an alternative could be a linear or higher order interpolation algorithm).

Figure 4:
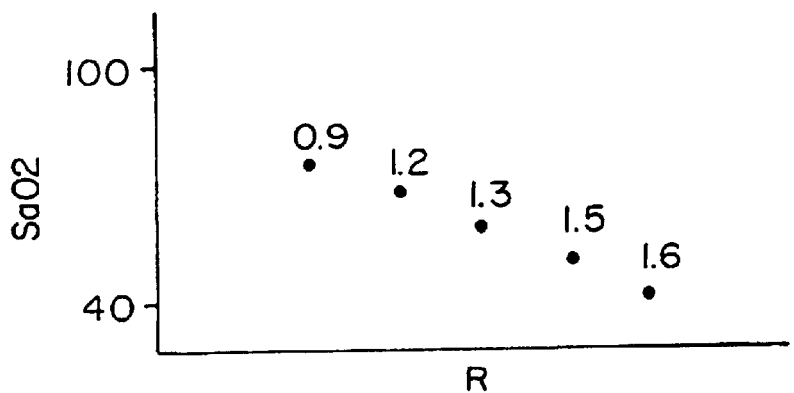
FIG. 4 is a graph of oxygen saturation versus R to illustrate the embodiment for spline or curve fitting to a predefined set of knots.

FIG. 4 illustrates the cubic spline method. FIG. 4 is a graph of oxygen saturation vs. R for a particular sensor emitter. Thus, instead of storing the coefficients as in the prior art method, the actual R or oxygen saturation values are calculated and stored in the sensor memory for that particular sensor's characteristics (e.g., emitter wavelengths). When the oximeter measures the signal level of the light detector, it determines an oxygen saturation value by determining the point on the curve associated with the calculated R value between two of the sample points shown in FIG. 4.

There exists a trade-off in the number of knots defined and the amount of memory required to store them. Too few knots requires very little storage memory, but may not adequately describe the functional relationship; too many over-defines the curve and consumes more memory. The inventors have found that knots spaced 5%–10% apart give adequate results.

Cubic Spline Calculation

The process for cubic spline interpolation is known to those skilled in the art. Intrinsic in using the spline method is that the value of R needs to be determined first before being translated to $SpO_2$. The preferred process for spline interpolation can be accomplished using the functions provided in Mathcad, and treats the endpoints with cubic functions. Other references for cubic spline interpolations are available.

The process of finding the coordinates of the knots in empirical data with a significant amount of noise may require an additional step. Commercially available basic curve fitting programs may be used (sigmaplot, or TableCurve, or Mathematical for instance) to determine a best-fit functional approximation to the data. Alternately, one can perform a least-squares fit of an arbitrarily chosen analytical function and pick the values of R at the knot locations ($SaO_2$ values). The analytical function can be an overlapping piece-wise polynomial (e.g., linear or parabolic), or the curvilinear equation of Eq. 1 or Eq. 4. Another approach is to perform a least-squares selection of the knots directly.

Figure 5A:
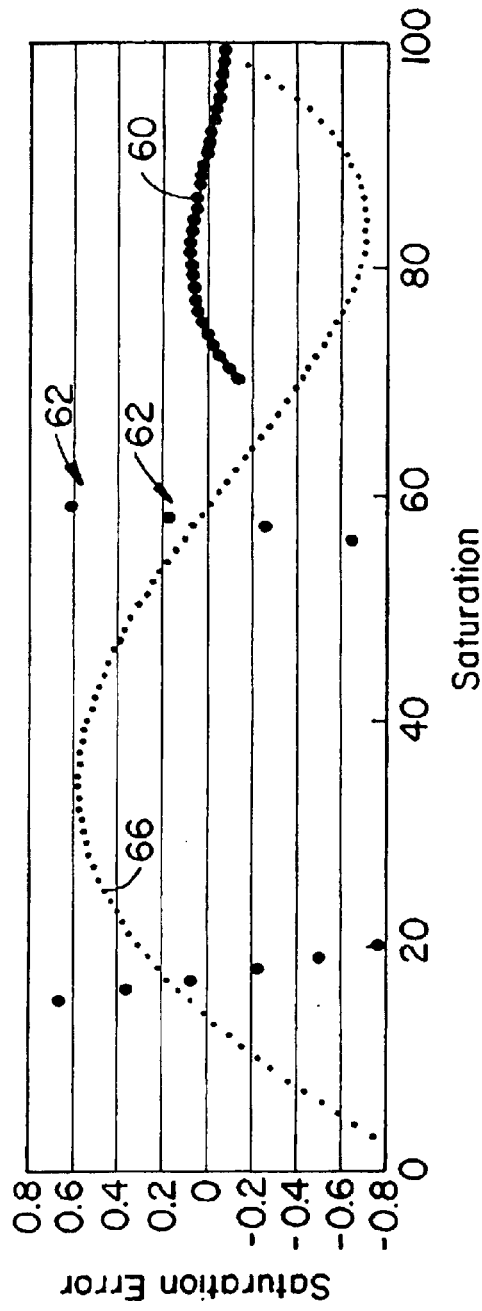
FIGS. 5A, 5B, 6A and 6B are graphs illustrating the improved curve fitting of the embodiments of the invention versus the prior art.
Figure 5B:
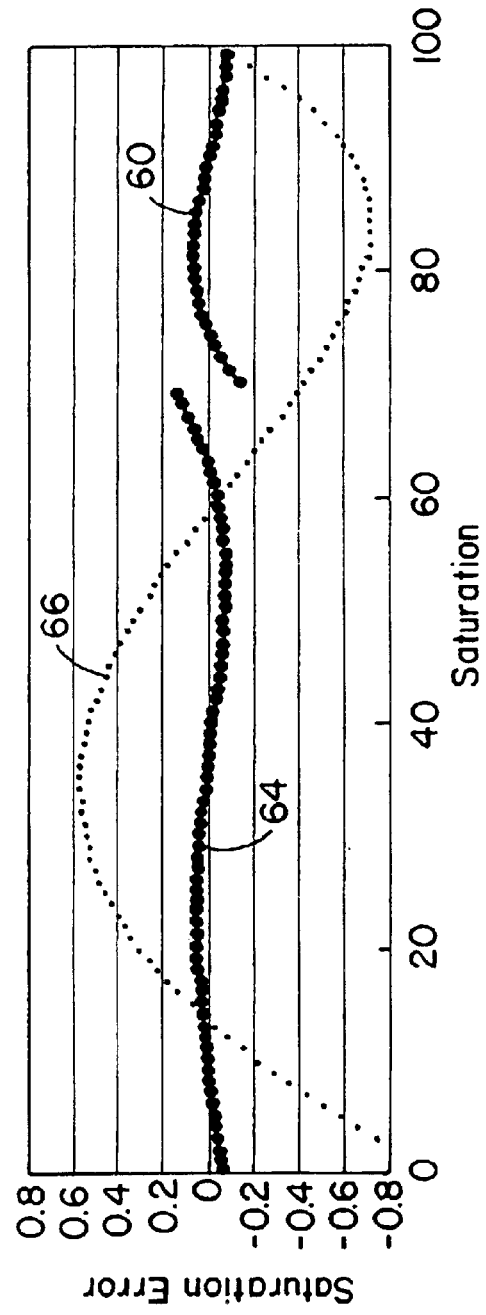

FIG. 5A shows the conventional curve fitting of the prior art, wherein a linear relationship is used below 70% saturation, with a curvilinear approach above 70%. The residual error due to an imperfect fit to the actual R to $SaO_2$ response for the curvilinear approach above 70% saturation is illustrated by curve 60, while the residual error of the linear interpolation approach below 70% is illustrated by dots 62. FIG. 5B illustrates the use of curvilinear fits in both regions, with a different curvilinear curve 64 being used below 70%. In this instance, a much improved fit is provided. In both figures, the smaller dotted line 66 corresponds to the use of a single curvilinear fit across both regions, which is also not as accurate, having a much higher error characteristic compared to the curves of the invention, 64 and 60 of FIG. 5B.

Figure 6A:
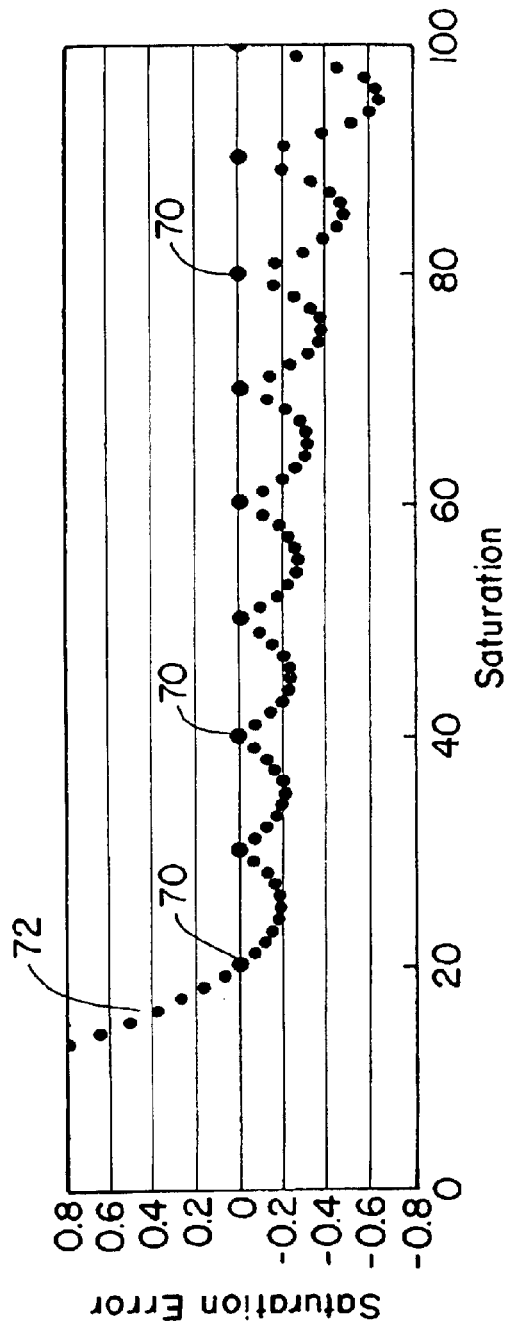
Figure 6B:
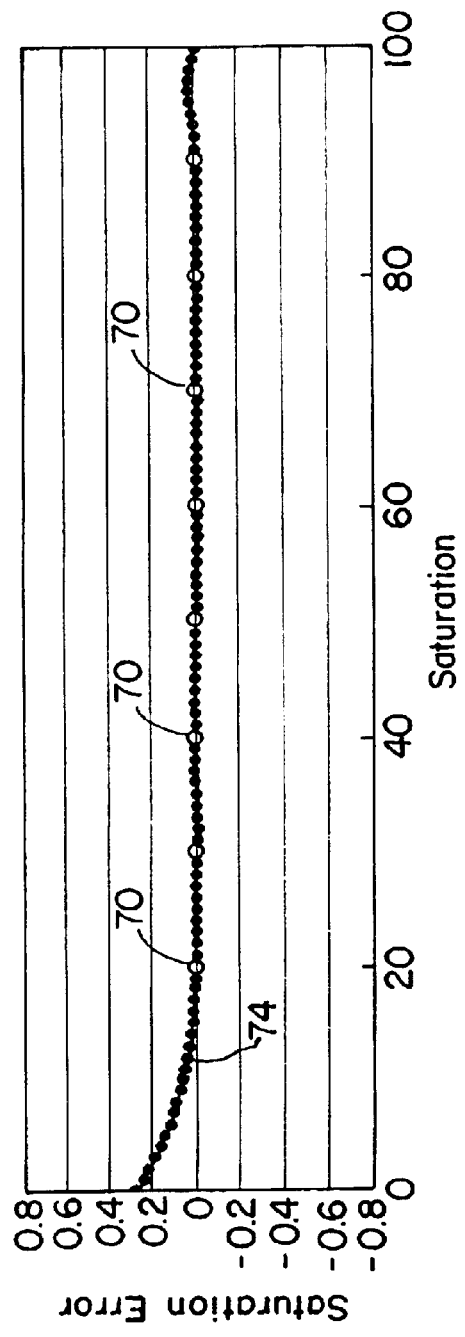

FIG. 6A and 6B show a plurality of knots as circles 70 on the graphs. Dotted line 72 of FIG. 6A illustrates a linear interpolation fit to these knots, which shows a residual error prone result with multiple loops. In FIG. 6B, on the other hand, the present invention using a cubic spline fitting approach provides a dotted line 74 which is a more accurate fit to the knots 70.

As will be understood by those of skill in the art, the present invention may be embodied in other specific embodiments without departing form the essential characteristics thereof. For example, any function can be used for the formulas for determining oxygen saturation, not just the ones described. For a limited sensor memory, the function representation may be compressed. Any representation of a function could be used. Calibration coefficients may be based on more or different characteristics than the sensor's LED wavelength(s). For example, other LED emitter characteristics or sensor design characteristics can be factors in the sensor's calibration coefficients.

Additionally, the formula for calculating oxygen saturation may be a function of more than the ratio of ratios; for example, other input variables such as signal strength, light levels, and signals from multiple detectors could be used.

This methodology for piece-wise fitting is not limited to oximetry. This method is useful when the relationship between the measured signal and reference value observed during calibration is not adequately described by a single function or set of coefficients over the whole measurement range. The relationship may be broken into subsets, and a piece-wise continuous set of functions may be used to describe the relationship. For example, other blood or tissue constituents could be calculated, such as carboxyhemoglobin, methemoglobin, bilirubin, glucose, lactate, etc. Accordingly, the foregoing description is intended to be illustrative, but not limiting, of the scope of the invention which is set forth in the following claims.

What is claimed is:

1. An oximeter sensor comprising:
   a light emitter for directing light at a patient;
   a light detector mounted to receive light from said patient; and
   a memory storing coefficients for use in at least one formula for determining oxygen saturation, said coefficients including at least a first set of coefficients and a second set of coefficients for said light emitter; wherein said first and second sets of coefficients are used in the same formula.

2. The oximeter sensor of claim 1 wherein said coefficients are dependent on a mean wavelength of said light emitter.

3. The oximeter sensor of claim 1 wherein said memory further stores a value indicating a signal breakpoint between said first and second sets of coefficients.

4. An oximeter sensor comprising:
   a light emitter for directing light at a patient;
   a light detector mounted to receive light from said patient; and
   a memory storing coefficients for use in at least one formula for determining oxygen saturation, said coefficients including at least a first set of coefficients and a second set of coefficients for said light emitter; wherein said first and second sets of coefficients are used in different formulas; wherein said different formulas are nonlinear formulas.

5. An oximeter sensor comprising:
   a light emitter for directing light at a patient;
   a light detector mounted to receive light from said patient; and
   a memory storing coefficients for use in at least one formula for determining oxygen saturation, said coefficients including at least a first set of coefficients and a second set of coefficients for said light emitter; wherein said first and second sets of coefficients are used in different formulas; wherein said different formulas are linear formulas.

6. An oximeter sensor comprising:
   a light emitter for directing light at a patient;
   a light detector mounted to receive light from said patient; and
   a memory storing coefficients for use in a formula for determining oxygen saturation, said coefficients including a first set of coefficients and a second set of coefficients,
   said memory further storing an indication of a saturation for use in selecting between said first and second sets of coefficients; wherein said first and second sets of coefficients are used in the same formula.

7. The oximeter sensor of claim 6 wherein said coefficients are dependent on a mean wavelength of said light emitter.

8. An oximeter system comprising:
   an oximeter sensor comprising
   a light emitter for directing light at a patient;
   a light detector mounted to receive light from said patient; and
   a memory storing a plurality of alternate values of oxygen saturation or signal ratiometric values used to determine oxygen saturation, said plurality of values being dependent on a mean wavelength of said light emitter; and
   an oximeter in communication with said oximeter sensor for receiving said plurality of values and a light detector signal, said oximeter being programmed to determine oxygen saturation from said light detector signal by fitting said oxygen saturation to a curve defined by said values stored in said memory.

* * * * *

UNITED STATES PATENT AND TRADEMARK OFFICE
CERTIFICATE OF CORRECTION

PATENT NO. : 6,801,797 B2  
APPLICATION NO. : 09/836050  
DATED : October 5, 2004  
INVENTOR(S) : Paul D. Mannheimer It is certified that error appears in the above-identified patent and that said Letters Patent is hereby corrected as shown below:

Immediately after the title, the following should be inserted:

--This application claims the benefit of U.S. Provisional Application No. 60/198,109, filed on April 17, 2000.--

Signed and Sealed this

Twenty-ninth Day of August, 2006

JON W. DUDAS  
*Director of the United States Patent and Trademark Office*